(12) United States Patent
Avakov

(10) Patent No.: US 10,175,151 B2
(45) Date of Patent: Jan. 8, 2019

(54) ENVIRONMENTAL MONITORING UAV SYSTEM

(71) Applicant: Yaaqov Avakov, Arad (IL)

(72) Inventor: Yaaqov Avakov, Arad (IL)

(73) Assignee: Yaaqov Avakov, Arad (IL)

( * ) Notice: Subject to any disclaimer, the term of this patent is extended or adjusted under 35 U.S.C. 154(b) by 0 days.

(21) Appl. No.: 15/574,311

(22) PCT Filed: May 17, 2016

(86) PCT No.: PCT/IL2016/050518
§ 371 (c)(1),
(2) Date: Nov. 15, 2017

(87) PCT Pub. No.: WO2016/185467
PCT Pub. Date: Nov. 24, 2016

(65) Prior Publication Data
US 2018/0136093 A1    May 17, 2018

Related U.S. Application Data

(60) Provisional application No. 62/162,978, filed on May 18, 2015.

(51) Int. Cl.
| G06F 19/00 | (2018.01) |
| G01N 1/22 | (2006.01) |
| G01N 1/20 | (2006.01) |
| B64C 39/02 | (2006.01) |
| B64D 1/00 | (2006.01) |

(52) U.S. Cl.
CPC ......... *G01N 1/2273* (2013.01); *B64C 39/024* (2013.01); *B64D 1/00* (2013.01); *G01N 1/20* (2013.01); *B64C 2201/027* (2013.01); *B64C 2201/125* (2013.01); *B64C 2201/141* (2013.01); *G01N 1/2202* (2013.01); *G01N 2001/2279* (2013.01)

(58) Field of Classification Search
CPC ............ B64C 39/024; B64C 2201/141; G08G 5/0069
USPC ....................... 702/24, 13, 14, 182–185, 188
See application file for complete search history.

(56) References Cited

U.S. PATENT DOCUMENTS

| 4,226,115 A | 10/1980 | Williams |
| 7,998,731 B2 | 8/2011 | Daitch |
| 2001/0044595 A1 | 11/2001 | Reydel |
| 2004/0118222 A1 | 6/2004 | Cornish |
| 2006/0011776 A1 | 1/2006 | Maurer |
| 2011/0139665 A1 | 6/2011 | Madsen |
| 2013/0292512 A1 | 11/2013 | Erben |
| 2014/0277834 A1* | 9/2014 | Levien ................. B64C 39/024 701/2 |
| 2017/0003684 A1* | 1/2017 | Knudsen ................ G01N 21/51 |

* cited by examiner

*Primary Examiner* — Edward Raymond
(74) *Attorney, Agent, or Firm* — Posternak Blankstein & Lund LLP

(57) ABSTRACT

The present invention relates to an environmental monitoring UAV system comprises a drone provided with an air monitoring platform that is adapted for taking air sample(s) by enforcing air to flow through or into at least one sampling medium, during the flight of said drone.

8 Claims, 3 Drawing Sheets

ENVIRONMENTAL MONITORING UAV SYSTEM

FIELD OF THE INVENTION

The present invention relates to the field of environmental monitoring. More particularly, the invention relates to an Unmanned Aerial Vehicle (UAV) for autonomously providing air monitoring.

BACKGROUND OF THE INVENTION

An Unmanned Aerial Vehicle (UAV), such as a drone, has many civilian and military uses for various purposes, while taking advantage of the flight capabilities of UAVs that may operate with various degrees of autonomy, either under remote control by a human operator, or fully or intermittently autonomously, by onboard computer units. The present invention tends to focus on novel solution for environmental monitoring.

It is an object of the present invention to provide a drone which is capable of providing air and environmental monitoring.

Other objects and advantages of the invention will become apparent as the description proceeds.

SUMMARY OF THE INVENTION

The present invention relates to an environmental monitoring UAV system comprises a drone provided with an air monitoring platform that is adapted for taking air sample(s) by enforcing air to flow through or into at least one sampling medium, during the flight of said drone.

According to an embodiment of the invention, the air monitoring platform includes measurement sensors unit configured to read environmental parameters, thereby triggering to take the air sample(s) at specific locations when the readings of said measurement sensors unit are above a specific threshold level.

In another aspect the present invention relates to a method for monitoring the environment, comprising providing a drone with an air monitoring platform adapted for taking air sample(s) by enforcing air to flow through or into at least one sampling medium, during the flight of said drone.

According to an embodiment of the invention, the sampling medium is a container, in particular in form of a gas sampling bag or a vacuum canister.

According to an embodiment of the invention, the sampling medium is a gas detection tube or air filters.

According to an embodiment of the invention, the method further comprising providing an environmental sensory module adapted for performing measurements of concentration of impurities in air, wherein the measurements are used for triggering the air monitoring platform to take air sample(s) whenever the concentration of impurities in air is above a predetermined level.

According to an embodiment of the invention, the method further comprising using the measurements to automatically navigate the drone in order to search for areas in midair where the concentration of impurities in air is above the predetermined level, by using the measurement sensors unit for continuously measuring concentration of impurities in air and accordingly navigating the drone towards said areas.

According to an embodiment of the invention, the enforcing of air to flow into a sampling medium is done by pumping air.

According to an embodiment of the invention, the enforcing of air to flow through or into a sampling medium is done by applying air suction.

DETAILED DESCRIPTION OF THE INVENTION

As used herein the term "drone" may refer to any aircraft vehicle that is operated without an on-board human pilot. For example, drones may include, but are not limited to, UAVs, fixed-wing UAVs, airship, air balloon, a remotely piloted aircraft (RPA), a multirotor, and the like. These drones may utilize various modes of propulsion, hoovering and/or flight capabilities.

Reference will now be made to several embodiments of the present invention, examples of which are illustrated in the accompanying figures. Wherever practicable similar or like reference numbers may be used in the figures and may indicate similar or like functionality. The figures depict embodiments of the present invention for purposes of illustration only. One skilled in the art will readily recognize from the following description that alternative embodiments of the structures and methods illustrated herein may be employed without departing from the principles of the invention described herein.

Various exemplary embodiments relate to a drone. According to an embodiment of the present invention, the drone may include: a navigation unit configured to determine the location of the drone and navigate the drone to designated locations, an measurement sensors unit configured to read environmental parameters such as type of pollutions and measurement of pollutions concentrations, an air sampling module configured to monitor the environment, e.g., by inflating at least one air sampling bag with a sampled of the surrounding air or by using a vacuum canister, and a wireless network transceiver configured to periodically transmit the location of the drone and environmental readings to a remote monitoring system or station.

In various embodiments, the wireless network transceiver is further configured to receive navigation path information including designated locations.

Figure 1:
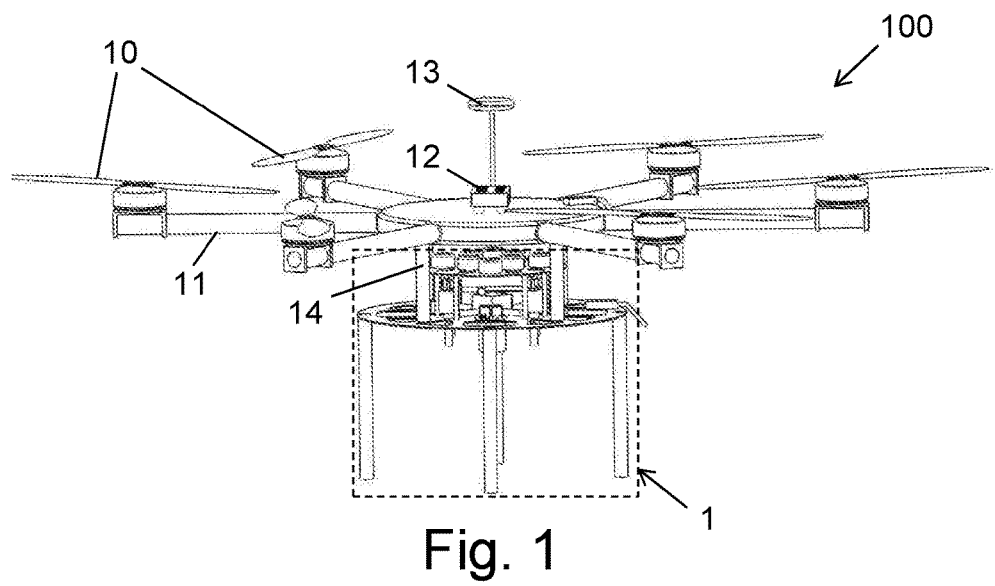
FIG. 1 schematically illustrates a drone provided with an air monitoring platform, according to an embodiment of the invention.

FIG. 1 schematically illustrates an exemplary drone 100 equipped with an air monitoring platform 1, according to an embodiment of the invention. Drone 100 may be a commercially available UAV platform that has been modified to carry specific modules and components of the air monitoring platform 1 as described in further detail below. Drone 100 may include rotors 10, motor support beams 11, and electronic units such as a flight controller 12 and a navigation module 13. Rotors 10 may provide lift for drone 100. As shown in FIG. 1, drone 100 may include four, six, eight or more rotors depending on the size and weight of the drone payload. For example, the number and size of the rotors may vary based on particular lift and flight time needs Drone 100 may further include a lower frame 14 that may provide a mounting point for attaching the air monitoring platform 1. In this figure, platform 1 is indicated by the dotted line.

In addition, Drone 100 may include electronic components (not shown) such as a battery for powering the drone's modules and components, a switch (e.g., such as a single throw multiple post switch for simultaneously switching power to each of the electronics components of the drone), wireless client (e.g., an industrial IEEE 802.11 wireless client or any other protocol), GPS receiver, a processor, and a memory. The processor may control operation of various computer programs on drone 100.

Figure 2:
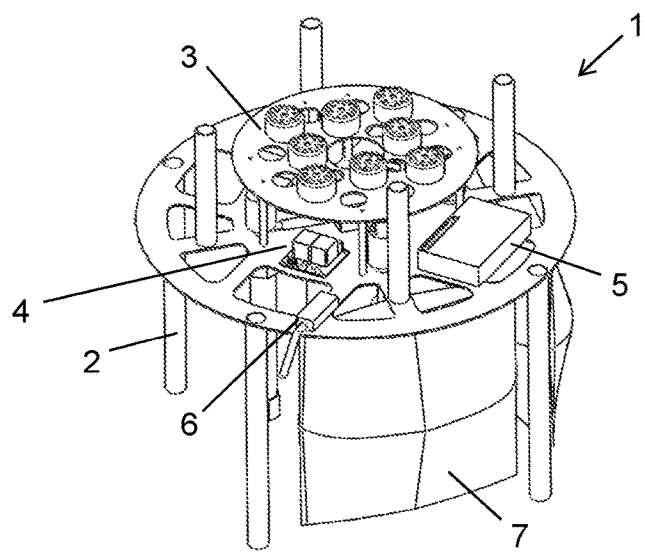
FIG. 2 schematically illustrates an air monitoring platform, according to an embodiment of the invention.

FIG. 2 schematically illustrates an air monitoring platform 1 adapted to be mounted or attached to drone 100, according to an embodiment of the invention. In some embodiments, air monitoring platform 1 can be an integral part of drone 100. For example, platform 1 can be connected to drone 100 mechanically via the lower frame 14 as shown in FIGS. 4-6 and electronically to the flight control module 12 of drone 100 via a microcontroller 5. Air monitoring platform 1 may include a supporting frame 2 on which measurement sensors unit 3, an air sampling unit 4, microcontroller 5 and a communication unit 6 are situated. The units of platform 1 are electronically communicated through the microcontroller 5. Platform 1 further comprises one or more sampling mediums, such as gas detection tubes (as indicated by numeral 18 in FIG. 3), gas sampling bags (as indicated by numeral 7 in FIG. 3), vacuum canisters (as indicated by numeral 9 in FIG. 3), air filters (as indicated by numeral 17 in FIG. 3) and the like. For example, in this figure a gas sampling bag 7 is shown.

Microcontroller 5 may be connected to measurement sensors unit 3, air sampling unit 4 and is also in data communication with the flight controller 12 of drone 100. Microcontroller 5 may receive data from measurement sensors unit 3, processes the receive data and accordingly activates air sampling unit 4. Microcontroller 5 may be communicatively coupled to a memory. In various embodiments, the microcontroller 5 may be integral with another electronic component, such as, for example, measurement sensors unit 3. In addition, microcontroller 5 may further communicate with a communication unit 6 (e.g., a wireless modem) for wirelessly communicating with a remote station (e.g., an environmental ground station 8 as shown in FIG. 3).

The memory may store a computer program or instructions for execution by the microcontroller 5. In various embodiments, the memory may store information for triggering/controlling the actuation of the air sampling unit 4 and additionally for providing navigation instructions to the flight controller 12 according to the readings of the measurement sensors unit 3, thereby, using drone 100 to automatically perform search for areas with highest concentration of impurities in air (e.g., areas in which the readings of the measurement sensors unit 3 are above a predetermined threshold level. The flight path of drone 100 is defined based on the readings of unit 3). The invention may also be practiced in distributed computing environments where tasks are performed by remote processing devices (e.g., a ground control station) that are linked through a communications network. In a distributed computing environment, program modules may be located in both local and remote memory storage devices. The functions described herein may be performed by executable code and instructions stored in the memory or other computer readable medium and running on the processor. However, state machines, and/or hardwired electronic circuits can also be utilized.

According to an embodiment of the invention, measurement sensors unit 3 may include one or more sensor or detectors (e.g., chemical sensors such as organic and inorganic, particle sensors such as p.m 10, Photoionization Detector (PID), radiation sensors, and the like). Measurement sensors unit 3 allows real-time monitoring information from the one or more sensors/detectors to be used as a trigger for actuating the air sampling unit 4. Measurement sensors unit 3 may also include an imaging system (e.g., camera) for transmitting visual information to a ground control station.

Figure 3:
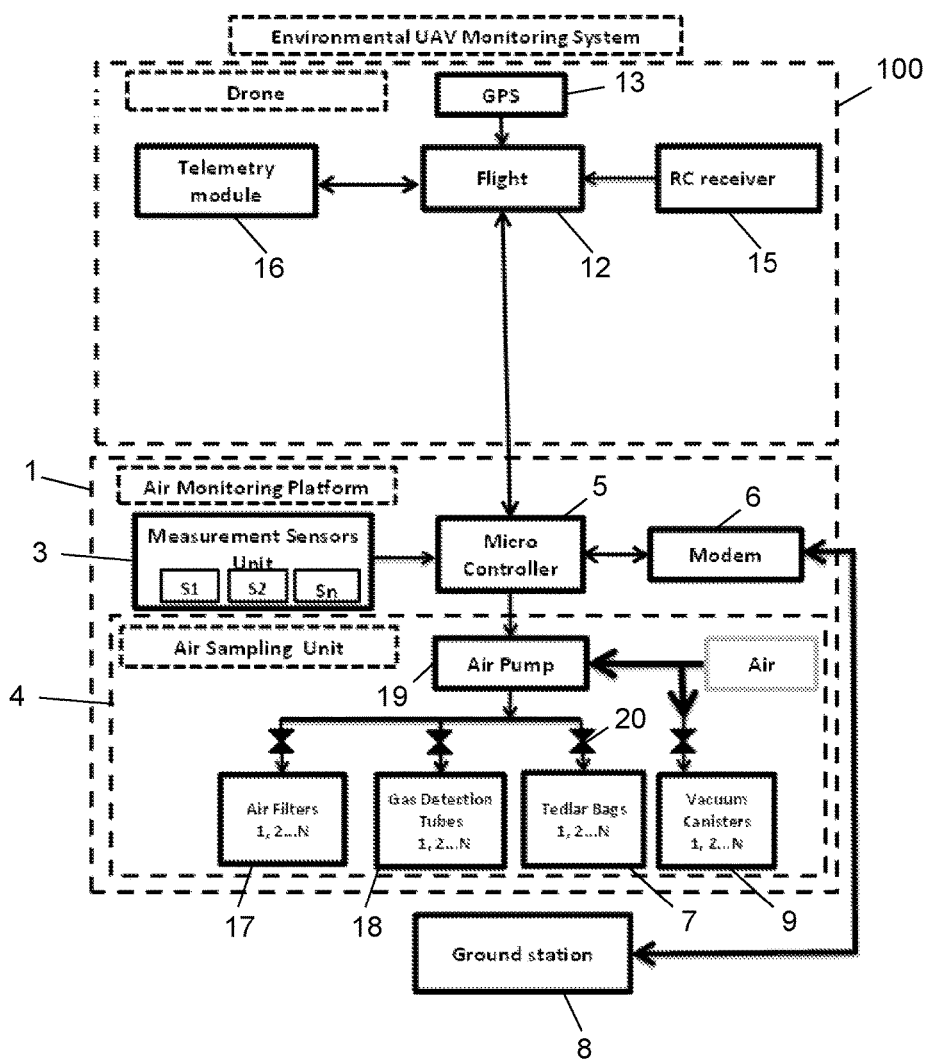
FIG. 3 is a schematic block diagram of an environmental UAV monitoring system, according to an embodiment of the invention.
Figure 4:
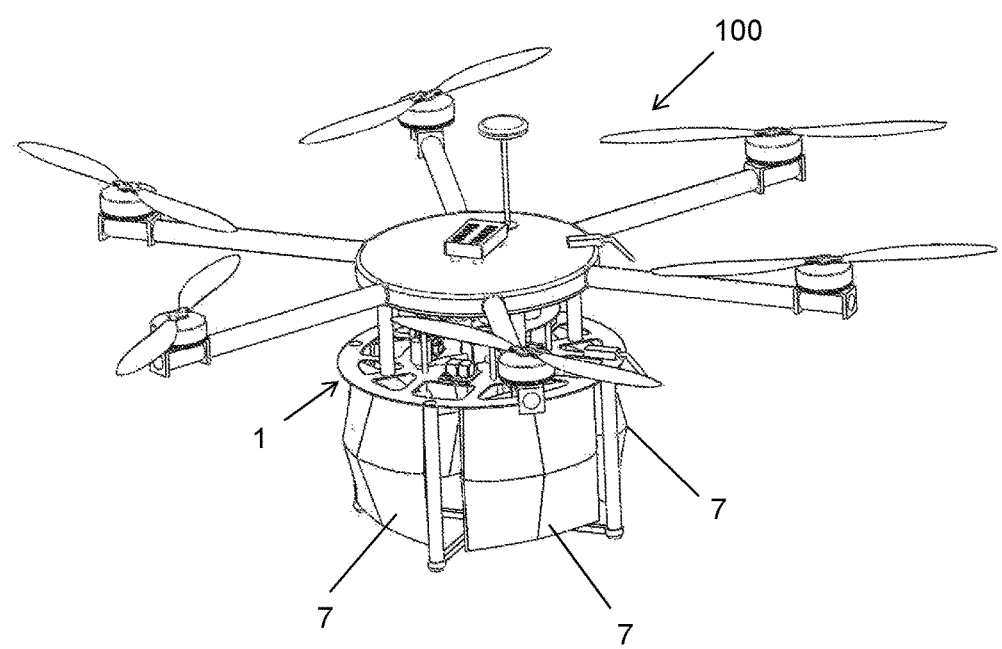
FIG. 4 shows the drone of FIG. 1 provided with with sampling bags in an inflated state.

Referring now to FIG. 3, a schematic block diagram of an environmental UAV monitoring system is shown in accordance with an embodiment of the invention. In the UAV monitoring system, air sampling unit 4 is configured to inflate at least one air sampling bag 7 (e.g., Tedlar® Gas Sampling Bags by DuPont™) with atmospheric gas of the surrounding air. Sampling unit 4 may include an electric air pump 19, and at least one sampling bag 7 provided with a bag valve 20 for enabling to inflate the bag 7. Air pump 19, and bag valve 20 are electronically controlled by microcontroller 5 that may receive information from unit 3 or from flight controller 12. In some embodiments, flight controller 12 can be used to activate air sampling unit 4 manually by receiving control signals via a remote control receiver 15 that can be operated by a human operator. A telemetry module 16 can be used to provide flight data an operator.

For example, air monitoring platform 1 may operate as follows:

receiving, by microcontroller 5, readings from measurement sensors unit 3 (e.g., readings that may indicate of a polluted area due to predetermined set of values);

if the readings values are above the predetermined set of values, actuating the air pump 19;

opening the bag valve 20 for a sampling time needed to fill bag 7 at least partially with sampled environmental air; and After the filling, closing the bag valve 20 and turning off the air pump 19.

At this stage, sampling bag 7 is filled with gas of the surrounding environment that may be suspicious as polluted.

In case of using more than one sampling medium (e.g., two or more sampling bags 7), a manifold (not shown) can be used to handle more than one sampling bag. The microcontroller 5 may control the inflating of each bag separately at different sampling location during the flight of the drone 100. FIG. 4 shows a drone provided with air monitoring platform 1 with several sampling bags 7 in an inflated state.

According to an embodiment of the invention, the flight controller 12 is in communication with a navigation module, which may be any receiver adapted for receiving location signals and determining a location. For example, the navigation module may include a GPS receiver for receiving GPS location signals and determining a location. In various embodiments, the navigation module may be integrated with a compass module and a drone navigation system. Alternatively, the processor and the memory may perform navigation based on data received from the navigation module. The navigation module may receive navigation path information stored in the memory or navigation path information provided via the wireless client. In various alternative embodiments, the navigation module may provide information to a human pilot who remotely controls drone 100 via the wireless client.

In some embodiments, the drone may also include safety module(s), such as avoidance or anti-collision system, an airbag system, etc.

All the above description and examples have been given for the purpose of illustration and are not intended to limit the invention in any way. Many different mechanisms, methods of analysis, electronic and logical elements can be employed, all without exceeding the scope of the invention.

The invention claimed is:

1. An environmental monitoring system for automatically searching for areas with high concentration of impurities in air configured to be mounted/attached to an unmanned aerial vehicle (UAV), comprising:
   a. a measurement. sensors unit configured to read environmental parameters; and
   b. a microcontroller for monitoring and controlling operation of said UAV and said measurement sensors unit; wherein said microcontroller receives readings from said measure t sensors unit and accordingly defining the flight path of said UAV based on readings of said measurement sensors unit.

2. A system according to claim 1, further comprising at least one air sampling unit with one or more sampling mediums, wherein samples of air arc collected by said air sampling unit.

3. A system according to claim 2, wherein readings of said measurement sensors unit that are above a specific threshold level trigger said air sampling unit to collect air sample(s).

4. A system according to claim 2, wherein at no of said one or more sampling mediums comprises a gas sampling bag and wherein samples of air collected by pumping air thereinto.

5. A system according to claim 2, wherein at least one of said on more sampling mediums comprises a vacuum canister and wherein samples of air are collected by applying air suction thereto.

6. A system according to claim 2, wherein the sampling medium comprises a gas detection tube or air filters.

7. A system according to claim 1, wherein the microcontroller provides instructions to the UAV to navigate in the direction of areas with high impurities.

8. A method for automatically searching for areas with high concentration of impurities in air, comprising:
   a. reading environmental parameters by a measurement sensors unit configured to be mounted/attached to a unmanned aerial vehicle (UAV)
   b. monitoring said measurement sensors unit by a microcontroller; and
   c. providing instructions, by said microcontroller, to said UAV for defining the flight path of said UAV based on readings said measurement sensors unit.

* * * * *